(12) United States Patent
Miller

(10) Patent No.: US 7,104,957 B2
(45) Date of Patent: Sep. 12, 2006

(54) METHODS AND SYSTEMS FOR ANGULAR-DEPENDENT BACKSCATTER SPATIAL COMPOUNDING

(75) Inventor: Steven Charles Miller, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 10/723,952

(22) Filed: Nov. 26, 2003

(65) Prior Publication Data

US 2005/0113695 A1    May 26, 2005

(51) Int. Cl.
   *A61B 8/00* (2006.01)
(52) U.S. Cl. .................................... 600/443
(58) Field of Classification Search ............... 600/443, 600/447, 454–456; 128/916; 73/625–626
   See application file for complete search history.

(56) References Cited

U.S. PATENT DOCUMENTS

| | | | |
|---|---|---|---|
| 4,272,991 A * | 6/1981 | Cribbs ........................ 73/621 |
| 4,418,575 A | 12/1983 | Hundt et al. | |
| 5,582,173 A * | 12/1996 | Li ............................ 600/443 |
| 6,117,081 A | 9/2000 | Jago et al. | |
| 6,126,598 A | 10/2000 | Entrekin et al. | |
| 6,210,328 B1 | 4/2001 | Robinson et al. | |
| 6,283,917 B1 | 9/2001 | Jago et al. | |
| 6,309,356 B1 | 10/2001 | Ustuner et al. | |
| 6,423,004 B1 | 7/2002 | Dong et al. | |
| 6,464,638 B1 | 10/2002 | Adams et al. | |
| 6,517,489 B1 | 2/2003 | Phillips et al. | |
| 6,524,252 B1 | 2/2003 | Yu et al. | |
| 6,527,720 B1 | 3/2003 | Ustuner et al. | |
| 6,544,177 B1 | 4/2003 | Robinson | |
| 6,547,732 B1 * | 4/2003 | Jago ........................ 600/437 |
| 6,551,246 B1 | 4/2003 | Ustuner et al. | |
| 6,692,439 B1 * | 2/2004 | Walker et al. ............. 600/443 |
| 6,705,993 B1 * | 3/2004 | Ebbini et al. ............. 600/443 |
| 6,858,010 B1 * | 2/2005 | Guracar et al. ............ 600/443 |
| 6,872,181 B1 * | 3/2005 | Tirumalai et al. .......... 600/447 |
| 6,951,540 B1 * | 10/2005 | Ebbini et al. ............. 600/437 |

* cited by examiner

*Primary Examiner*—Francis J. Jaworski
(74) *Attorney, Agent, or Firm*—Small Patent Law Group; Dean D. Small

(57) ABSTRACT

A method of medical ultrasonic imaging is provided. The method includes transmitting a plurality of ultrasonic waves into a volume such that each successive wave is transmitted into the volume at a steering angle different than each preceding transmitted wave, receiving a plurality of ultrasonic echoes for each of the plurality of transmitted ultrasonic waves, each received echo is indicative of a density interface within the volume, each set of received echoes that corresponds to a single transmitted wave defines a steering frame, combining steering frames into a compound image, and identifying distal shadows in each steering frame.

25 Claims, 4 Drawing Sheets

US 7,104,957 B2

METHODS AND SYSTEMS FOR ANGULAR-DEPENDENT BACKSCATTER SPATIAL COMPOUNDING

BACKGROUND OF THE INVENTION

The present invention relates to diagnostic ultrasound systems. In particular, the present invention relates to methods and apparatus for acquiring and processing ultrasound data to highlight artifacts in ultrasound images.

At least some known ultrasonic systems are capable of spatially compounding a number of ultrasound images of a given target that have been obtained from a plurality of steering angles. The images are combined into a single compounded image by combining the data received from each point in the compound image target which has been received from each steering angle. Real time spatial compound imaging may be performed by acquiring a series of partially overlapping component image frames from substantially independent steering angles. An array transducer may be utilized to implement electronic beam steering and/or electronic translation of the component frames. The component frames are combined into a compound image by summation, averaging, peak detection, or other combinational means. The compounded image may display relatively lower speckle and better specular reflector delineation than a non-spatially compounded ultrasound image from a single angle. Distal end shadows of attenuative objects in the field of view may also be reduced when using spatial compounding.

Further, spatial compound imaging may facilitate improving image quality by improving specular interface acquisition and reducing distal end shadows of objects in the field of view. For example, a density interface, or acoustic impedance may produce a strong echo when the ultrasound beam is exactly perpendicular to a surface of the interface, and a relatively weak echo when the beam is only a few degrees off perpendicular. Spatial compounding acquires views of the interface from a plurality of different angles, making the curved interface visible and continuous over a larger field of view and reducing the effects of distal end shadowing. However, simply removing specular interference and distal end shadows from the image may also remove valuable diagnostic information from the image.

Although spatial compounding may improve image quality by reducing and specular reflections and distal end shadows, spatial compounding may also reduce the viewing capability of bodies of interest within these areas.

BRIEF DESCRIPTION OF THE INVENTION

In one embodiment, a method of medical ultrasonic imaging is provided. The method includes transmitting ultrasonic waves into a volume at different steering angles, receiving ultrasonic echoes for each of the ultrasonic waves, each ultrasonic echo being indicative of a density interface within the volume wherein the ultrasonic echoes are organized into steering frames, identifying a distal shadow within at least one of said steering frames, and combining the steering frames into a compound image.

In another embodiment, an ultrasound system is provided. The system includes a transmitter for transmitting a plurality of ultrasonic waves into a volume such that each successive wave is transmitted into the volume at a steering angle different than each preceding transmitted wave, a receiver for receiving a plurality of ultrasonic echoes for each of the plurality of transmitted ultrasonic waves, each the received echo is indicative of a density interface within the volume, each set of received echoes that corresponds to a single transmitted wave defines a steering frame, a signal processor combining the steering frames into a compound image and identifying a distal shadow in each steering frame, and a display for outputting information based on the identified distal shadows.

In yet another embodiment, a computer program embodied on a computer readable medium for controlling medical ultrasonic imaging is provided. The program includes a code segment that transmits a plurality of ultrasonic waves into a volume such that each successive wave is transmitted into the volume at a steering angle different than each preceding transmitted wave, receives a plurality of ultrasonic echoes for each of the plurality of transmitted ultrasonic waves, each received echo is indicative of a density interface within the volume, each set of received echoes that corresponds to a single transmitted wave defines a steering frame, combines steering frames into a spatially compounded image, and identifies distal shadows in each steering frame.

DETAILED DESCRIPTION OF THE INVENTION

Figure 1:
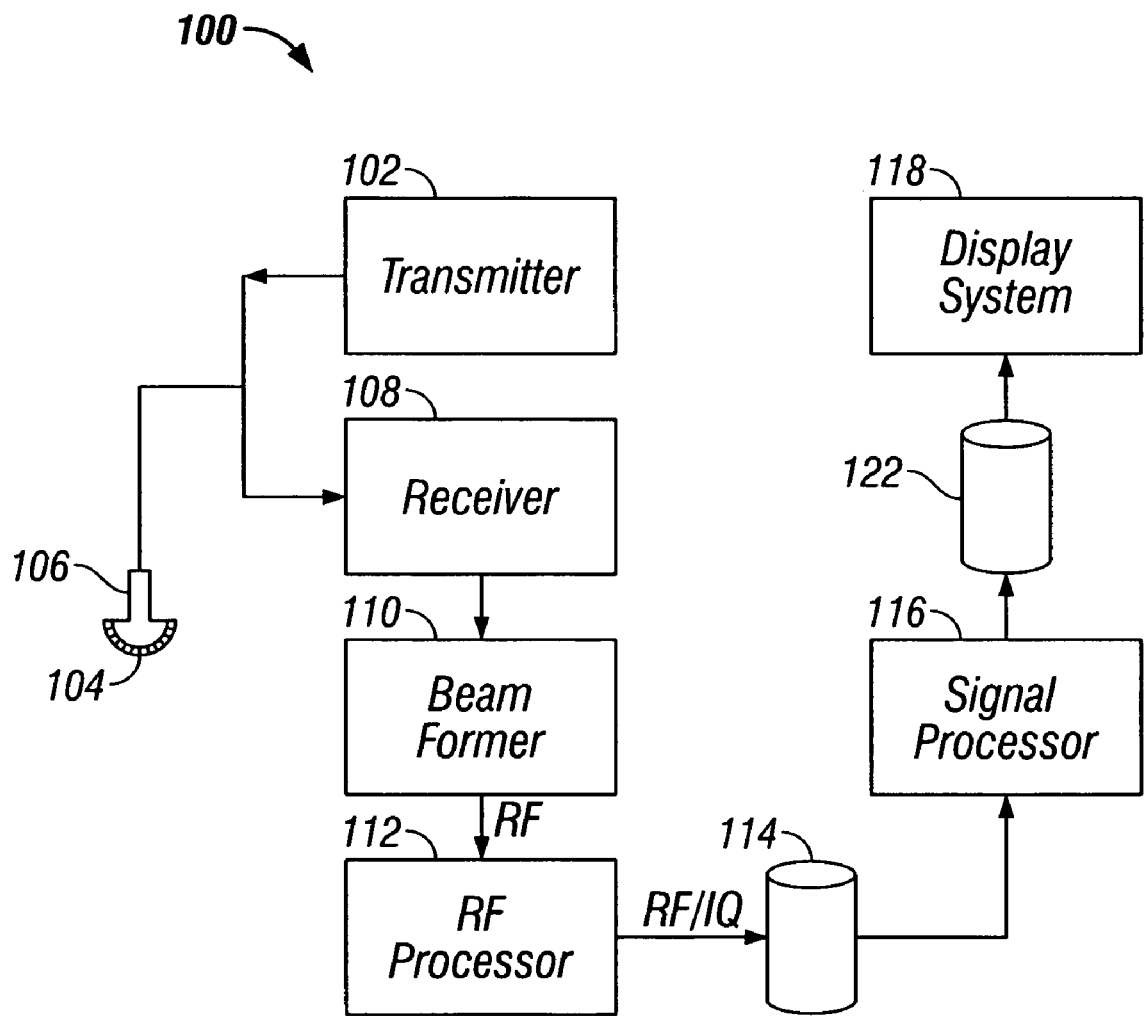
FIG. 1 is a block diagram of an exemplary ultrasound system.

FIG. 1 is a block diagram of an exemplary ultrasound system 100. Ultrasound system 100 includes a transmitter 102 which drives a n array of elements 104 within a probe 106 to emit pulsed ultrasonic signals into a body. A variety of geometries may be used. The ultrasonic signals are back-scattered from density interfaces and/or structures in the body, like blood cells or muscular tissue, to produce echoes which return to elements 104. The echoes are received by a receiver 108. The received echoes are passed through a beamformer 110, which performs beamforming and outputs an RF signal. The RF signal then passes through an RF processor 112. Alternatively, RF processor 112 may include a complex demodulator (not shown) that demodulates the RF signal to form IQ data pairs representative of the echo signals. The RF or IQ signal data may then be routed directly to RF/IQ buffer 114 for temporary storage.

Ultrasound system 100 also includes a signal processor 116 to process the acquired ultrasound information (i.e., RF signal data or IQ data pairs) and prepare frames of ultrasound information for display on display system 118. Signal processor 116 is adapted to perform one or more processing operations according to a plurality of selectable ultrasound modalities on the acquired ultrasound information. In the exemplary embodiment, acquired ultrasound information is processed in real-time during a scanning session as the echo signals are received. In an alternative embodiment, the ultrasound information may be stored temporarily in RF/IQ buffer 114 during a scanning session and processed in less than real-time in a live or off-line operation.

Ultrasound system 100 may continuously acquire ultrasound information at a frame rate that exceeds fifty frames per second, which is approximately the perception rate of the human eye. The acquired ultrasound information is displayed on display system 118 at a slower frame-rate. An image buffer 122 is included for storing processed frames of acquired ultrasound information that are not scheduled to be displayed immediately. In the exemplary embodiment, image buffer 122 is of sufficient capacity to store at least several seconds worth of frames of ultrasound information. The frames of ultrasound information are stored in a manner to facilitate retrieval thereof according to its order or time of acquisition. Image buffer 122 may include at least one memory device, such as, but not limited to, a read only memory (ROM), a flash memory, and/or a random access memory (RAM) or other known data storage medium.

Figure 2:
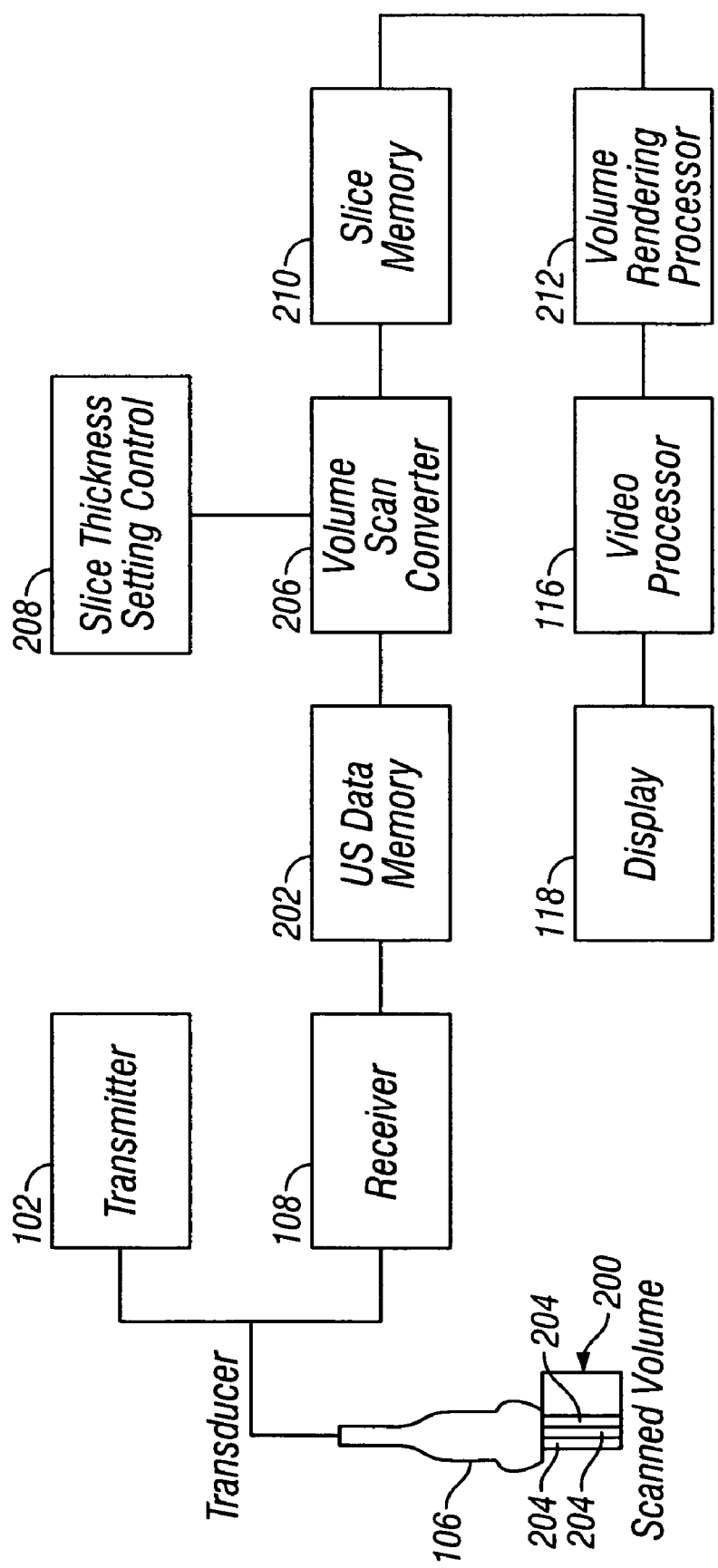
FIG. 2 is another block diagram of the exemplary ultrasound system shown in FIG. 1 that may be used to acquire and process ultrasonic images.

FIG. 2 is another block diagram of the exemplary ultrasound system 100 (shown in FIG. 1) that may be used to acquire and process ultrasonic images. System 100 includes probe 106 connected to transmitter 102 and a receiver 108. Probe 106 transmits ultrasonic pulses and receives echoes from structures inside of a scanned ultrasound volume 200. A memory 202 stores ultrasound data from receiver 108 derived from scanned ultrasound volume 200. Volume 200 may be obtained by various techniques, for example, but not limited to, 3D scanning, real-time 3D imaging, volume scanning, 2D scanning with transducers having positioning sensors, freehand scanning using a Voxel correlation technique, 2D or matrix array transducers.

Probe 106 is moved, such as along a linear or arcuate path, while scanning a region of interest (ROI). At each linear or arcuate position, probe 106 obtains a plurality of scan planes 204. Scan planes 204 are collected for a thickness, such as from a group or set of adjacent scan planes 204. Scan planes 204 are stored in memory 202, and then passed to a volume scan converter 206. In some embodiments, probe 106 may obtain lines instead of scan planes 204, and memory 202 may store lines obtained by probe 106 rather than scan planes 204. Volume scan converter 206 may store lines obtained by probe 106 rather than scan planes 204. Volume scan converter 206 receives a slice thickness setting from a control input 208, which identifies the thickness of a slice to be created from scan planes 204. Volume scan converter 206 creates a data slice from multiple adjacent scan planes 204. The number of adjacent scan planes 204 that are obtained to form each data slice is dependent upon the thickness selected by slice thickness control input 208. The data slice is stored in a slice memory 210 and is accessed by a volume rendering processor 212. Volume rendering processor 212 performs volume rendering upon the data slice. The output of volume rendering processor 212 is passed to video processor 116 and display 118.

Figure 3:
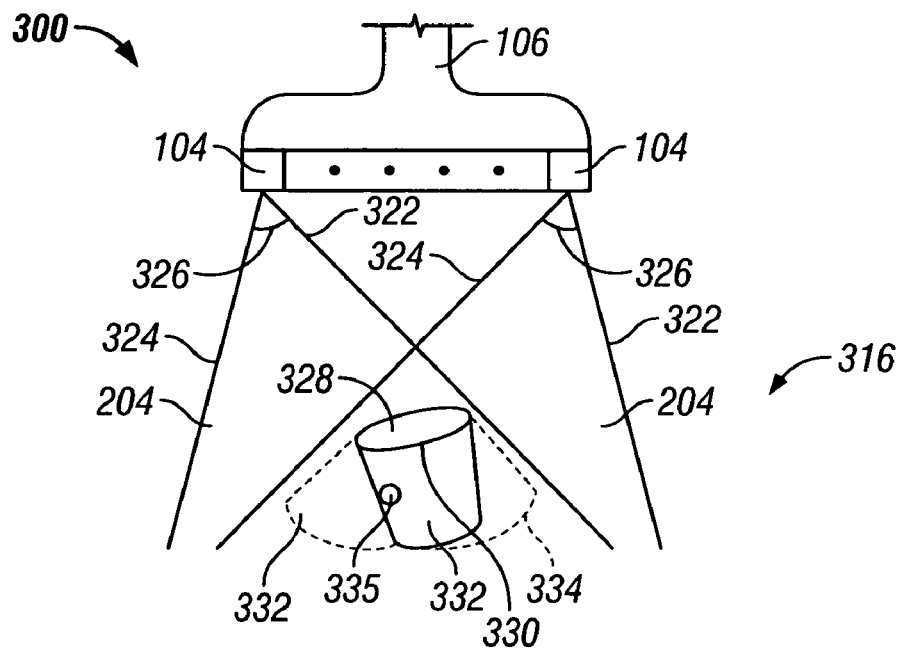
FIG. 3 illustrates an exemplary display 300 of an object acquired by the ultrasound system shown in FIG. 1.

FIG. 3 illustrates an exemplary display 300 of an object acquired by system 100 (shown in FIG. 1). Volume 316 includes a plurality of sector shaped cross-sections with radial borders 322 and 324 diverging from one another at an angle 326. Probe 106 electronically focuses and directs ultrasound firings longitudinally to scan along adjacent scan lines in each scan plane 204 and electronically or mechanically focuses and directs ultrasound firings laterally to scan adjacent scan planes 204. Scan planes 204 obtained by probe 106 are stored in memory 202 and are scan converted from spherical to Cartesian coordinates by volume scan converter 206. A volume comprising multiple scan planes is output from volume scan converter 206 and stored in slice memory 210.

Echo images from a body 328 with the region of interest may partially or completely obscure a volume in the region of interest toward a side 330 of body 328 that is distal from array of elements 104. Such an obscured area, or distal shadow 332, may contain data of interest that may be otherwise indiscernible due to the effects of distal shadow 332. As elements 104 scans volume 316 with a plurality of adjacent scan planes 204, distal shadow 332 effectively moves with respect to stationary body 328. System 100 detects such relative motion of distal shadows 332 and based thereon identifies an area 334 that potentially includes a distal shadow 332 within volume 316. The identified area 334 is evaluated to determine the presence of distal shadows 332 or other artifacts. In the exemplary embodiment, a position and orientation of potential distal shadows are back calculated to determine an origin of the shadow. For example, an exponential back calculation may reveal that the source of distal shadow 332 is body 328.

Additional calculations evaluating the attenuating characteristics of body 328 may be used to facilitate verifying that body 328 is the source of distal shadow 332. When distal shadow 332 is verified, a highlighting attribute is enabled to highlight area 334 that has been determined to be distal shadow 332. In one embodiment, the highlighting includes outlining area 334. In an alternative embodiment, highlighting includes illuminating area 334 in reverse video. In another alternative embodiment area 334 is tinted to distinguish it from other areas. The highlighting attribute is selectable based on a user's preference. Highlighting is available to facilitate determining the presence of an area of interest that may be partially or completely indiscernible due to a body or other structure creating an obscured area on the distal side of the body or structure from elements 104. Highlighting may be disabled once distal shadow 332 has been identified and displayed.

Distal shadow 332 may be differentiated from a distal object 334 in distal shadow 332, and use the presence of distal shadow 332 to characterize body 328 creating distal shadow 332. A relative attenuation of body 328 may result in distal shadow 332 being darker or brighter than volume 316. For example, a highly attenuative body 328 may create a relatively dark distal shadow 332 because of scattering and/or absorption. In the case of scattering, body 328 may appear relatively bright with a dark shadow. In the case of absorption, body 328 may not appear any brighter than volume 316. Distal shadow 332 may be indistinguishable from hypoechoic tissue, for example, but not limited to cystic or fluid filled regions. If body 328 has a relatively low attenuation rate, its distal shadow 332 may be brighter than volume 316, a situation called "acoustic enhancement." When distal shadow 332 is relatively brighter than volume 316, distal shadow 332 may be interpreted as an object of interest, such as distal object 334. In such a case, body 328, which is creating the bright distal shadow 332 may or may not be distinguishable depending if the bright distal shadow 332 is a result of low scattering or low absorption, respectively.

System 100 may selectably highlight distal shadow regions 332 to aid a user to determine whether distal object 328 is a real object or only an artifact. Highlighted distal shadow 332 may also be used to diagnose body 328 creating highlighted distal shadow 332. For example, an acoustic enhancing distal shadow 332 proximate to a dark body 328 may indicate body 328 is a benign cyst. However if there is no enhancement of distal shadow 332, or distal shadow 332 is dark, then the object may be suspect. The outline of distal shadow 332 may be identified by a difference between image frames. Filtering may be used to reduce speckle in each frame and then a composite deviation frame may be formed based on a standard deviation of each respective pixel from image frame to image frame. The deviation frame may selectively highlight the boundaries of the sector shaped distal shadow 332 with an apex centered on body 328 creating the shadow. This shadow highlight frame may be used to highlight distal shadow 332 on the composite image. Additional processing, such as, morphological filtering may be used to provide an outline of distal shadow 332 and to identify and highlight a source of distal shadow 332.

Figure 4:
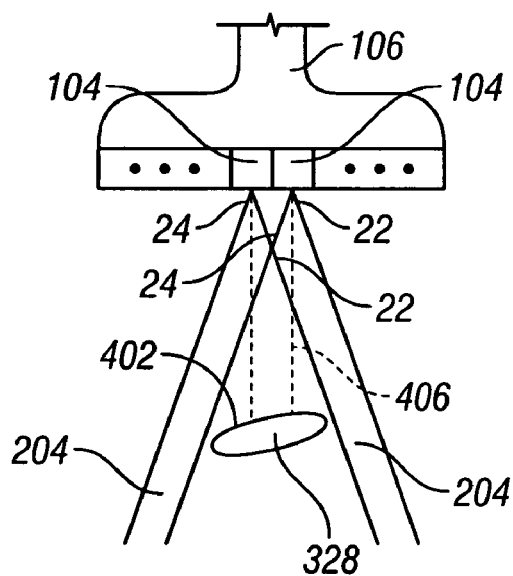
FIG. 4 illustrates another exemplary object acquired by the ultrasound system shown in FIG. 1.

FIG. 4 illustrates another exemplary object acquired by system 100 (shown in FIG. 1). During scanning, a portion of each scan plane 204 may intersect a portion of body 328 orthogonally such that the ultrasonic wave is projected to an area 402 of body 328 that is perpendicular to the incoming ultrasonic wave. In such a case, the wave is reflected directly back into probe 106. For example, a portion of scan plane that follows a path of a line 406 that is normal to probe 106 may reflect directly back to probe 106. Accordingly, a greater portion of the ultrasonic energy will be returned to probe 106 from that point than other points that are not located on paths that are normal to probe 106. The intensity of reflections from areas of body 328 that are not orthogonal to probe 106 may be less than the intensity of reflections from area 402 that is orthogonal to probe 106. The higher intensity reflections may appear relatively brighter on display 118. Such an increased brightness area may be perceived, by a user, as an indication and/or may obscure an indication, which may be of interest to the user.

System 100 detects such potential indications 404 and determines whether the indication is due to an orthogonal reflection based on an angle of incidence of the reflected wave. In one embodiment, system 100 compares reflections from a potential indication and areas adjacent to the potential indication. In an alternative embodiment, system 100 uses timing of reflections from a potential indication and areas adjacent to the potential indication to verify orthogonal potential indications. In the case of specular boundaries, a bright spot may be an artifact, a scattering object, or tissue that is composed of specular surfaces, such as, for example muscle striation. A similar method as for shadowing may can be used to differentiate between these possibilities however, speckle reduction may be performed on the composite deviation frame rather than the input frames. The specular boundaries of the compound image may then be highlighted with tinting, for example.

When potential indication 404 is verified, a highlighting attribute is enabled to highlight the area determined to be the potential indication 404. The highlighting attribute is selectable based on a user's preference. Highlighting is available to facilitate determining the presence of an area of interest that may be partially or completely indiscernible due to creating a false indication or obscuring an indication between the body 328 or structure and elements 104. Highlighting may be disabled once the potential indication 404 has been identified and displayed.

Figure 5:
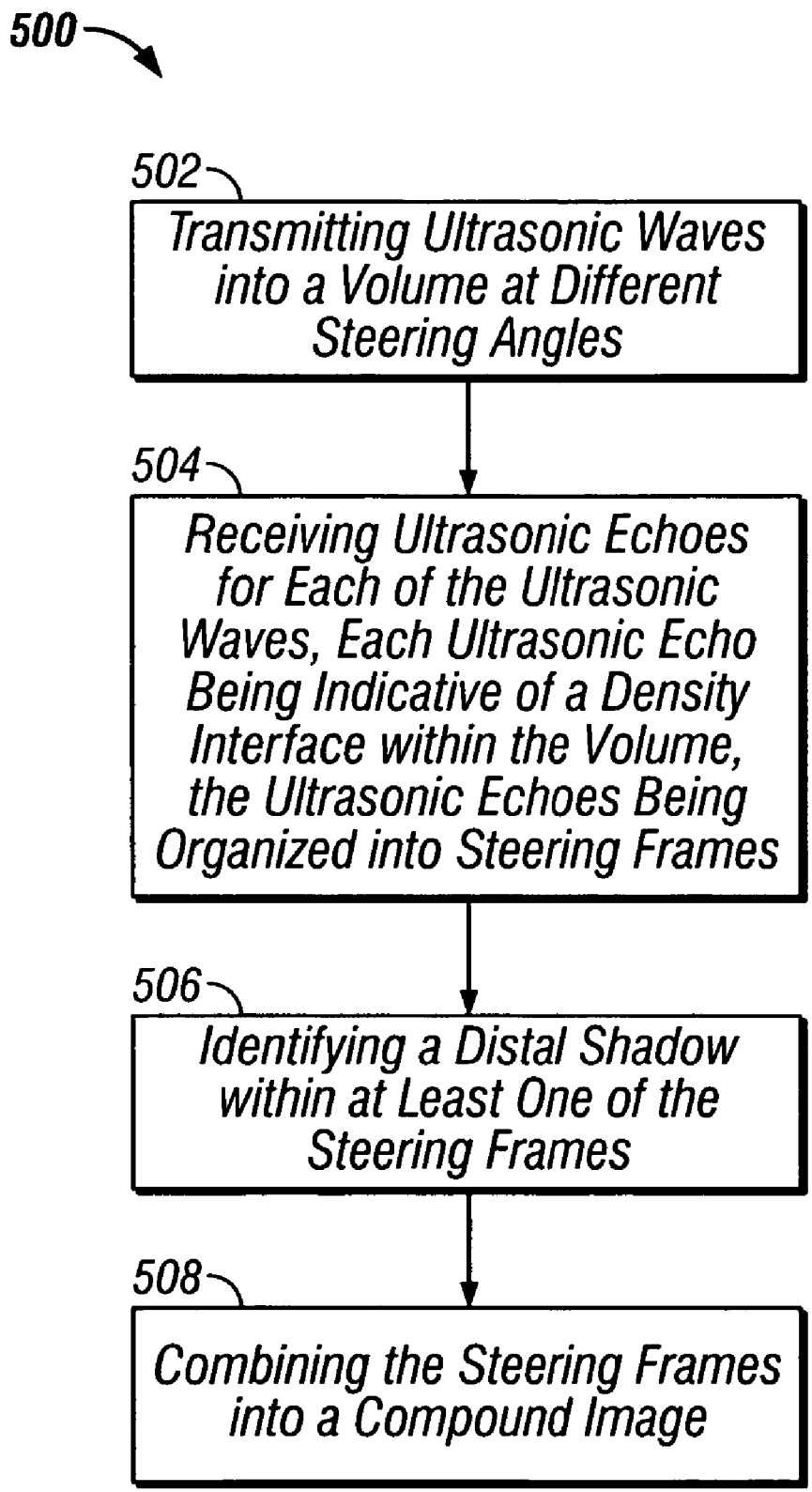
FIG. 5 is a block diagram of an exemplary method for acquiring and processing images using the ultrasound system shown in FIG. 1.

FIG. 5 is a block diagram of an exemplary method 500 for acquiring and processing images using system 100 (shown in FIG. 1). Method 500 includes transmitting (step 502) ultrasonic waves into volume 316 (shown in FIG. 3) at different steering angles. In the exemplary embodiment, volume 316 is a human body. In an alternative embodiment, the volume is any volume of interest that is interrogatable with ultrasonic waves. System 100 receives (step 504) a plurality of ultrasonic echoes for each of the plurality of transmitted ultrasonic waves. Each received echo is indicative of a density interface within volume 316. Each set of received echoes that corresponds to a single transmitted wave defines a steering frame. System 100 combines, at step 506, steering frames into a compound image and identifies, at step 508, distal shadow 332 in each steering frame. In the exemplary embodiment, each distal shadow 332 is highlighted so that the user may be alerted to an area of the image that may to identify an area that may be indicative of obscured echoes. A user may selectively identify such obscured areas or may disable the identification to view a standard compounded image. In an alternative embodiment, each distal shadow 332 is tinted to facilitate identifying an area which may be obscured from ultrasound view by distal shadow 332. Various tinting combinations may be selected by the user to facilitate localizing and determining the extent of distal shadow 332. Additionally, a location of the source of distal shadow 332 may be backcalculated from the distal shadow data, including a calculated attenuation factor, and/or the size and shape of the distal shadow. The backcalculation may utilize an exponential algorithm to determine the body responsible for creating distal shadow 332.

In another embodiment, system 10 identifies an area of substantially orthogonal echo reflection creating an area of brightness on display 118. The area of orthogonal reflection may be selectively highlighted and/or tinted to indicate areas of reflection to the user.

A technical effect of the distal shadow and specular reflection identification methods and systems described herein include at least one of facilitating improving diagnostic determination of attenuative objects within a field of view and improving determination of a source and characteristics of an acoustic impedance within the field of view.

The above-described angular-dependent backscatter spatial compounding method is cost-effective and highly reliable for locating, identifying and highlighting areas of distal shadow, which may obscure objects of interest in a spatially compounded ultrasonic image. Specifically, spatial compounding method facilitates combining ultrasonic images such that shadow areas, which may positioned behind an attenuative body relative to the ultrasonic transducer, are identified to the user in order that he user may investigate the area further. As a result, the methods and apparatus described herein facilitate ultrasonic imaging in a cost-effective and reliable manner.

Exemplary embodiments of diagnostic ultrasound systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method of medical ultrasonic imaging comprising:
   transmitting ultrasonic waves into a volume at different steering angles;
   receiving ultrasonic echoes for each of the ultrasonic waves, each ultrasonic echo being indicative of a density interface within the volume, said ultrasonic echoes being organized into steering frames;

identifying a distal shadow within at least one of said steering frames;

combining said steering frames into a compound image; and identifying an area of substantially orthogonal echo reflection from a density interface in one of the steering frames.

2. A method in accordance with claim 1 wherein said identifying the distal shadow comprises highlighting the distal shadows on the compound image.

3. A method in accordance with claim 2 wherein said highlighting step comprises selectively highlighting the distal shadows on a spatially compounded image display.

4. A method in accordance with claim 1 wherein said identifying the distal shadow comprises selectively tinting the distal shadows on the compound image.

5. A method in accordance with claim 1 further comprising identifying an area of substantially orthogonal echo reflection from a density interface in the remaining of the steering frames.

6. A method in accordance with claim 5 wherein identifying an area of substantially orthogonal echo reflection comprises highlighting the orthogonal echo reflection areas on the compound image.

7. A method in accordance with claim 1 wherein said identifying step comprises backcalculation echo reflection data to identify a source of the distal shadow.

8. A method in accordance with claim 1 wherein backcalculating echo reflection data to identify a source of the distal shadow comprises backcalculating echo reflection data using an exponential algorithm.

9. An ultrasound system, comprising:

a transmitter for transmitting ultrasonic waves into a volume at different steering angles;

a receiver for receiving ultrasonic echoes for each of said ultrasonic waves, each said ultrasonic echo being indicative of a density interface within the volume, said ultrasonic echoes being organized into steering frames;

a signal processor identifying a distal shadow in each steering frame, said signal processor combining said steering frames into a compound image; and a display for outputting information based on said identified distal shadows, wherein said system backcalculates echo reflection data to identify a source of the distal shadow.

10. An ultrasound system in accordance with claim 9 wherein said system highlights said distal shadows on an image display.

11. An ultrasound system in accordance with claim 10 wherein said system is configured to selectively highlight said distal shadows on an image display.

12. An ultrasound system in accordance with claim 9 wherein said system is configured to selectively tint the distal shadows on an image display.

13. An ultrasound system in accordance with claim 9 wherein said system is further configured to identify an area of substantially orthogonal echo reflection from a density interface in each steering frame.

14. An ultrasound system in accordance with claim 13 wherein said system highlights the orthogonal echo reflection areas on an image display.

15. An ultrasound system in accordance with claim 13 wherein said system tints the orthogonal echo reflection areas on an image display.

16. An ultrasound system in accordance with claim 9 wherein said system backcalculates echo reflection data using an exponential algorithm.

17. A computer program embodied on a computer readable medium for controlling medical ultrasonic imaging comprising, said program comprising a code segment that receives user selection input data and then:

transmits ultrasonic waves into a volume at different steering angles;

receives ultrasonic echoes for each of the transmitted ultrasonic waves, each received echo being indicative of a density interface within the volume, each ultrasonic echo being organized into steering frames;

identifies distal shadows in each steering frame;

combines steering frames into a spatially compounded image; and identifies an area of substantially orthogonal echo reflection from a density interface in one of the steering frames.

18. A computer program in accordance with claim 17 further comprising a code segment that highlights the distal shadows on the compounded image.

19. A computer program in accordance with claim 18 further comprising a code segment that selectively highlights the distal shadows on the compounded image.

20. A computer program in accordance with claim 17 further comprising a code segment that selectively tints the distal shadows on the compounded image.

21. A computer program in accordance with claim 17 further comprising a code segment that identifies an area of substantially orthogonal echo reflection from a density interface in the remaining of the steering frames.

22. A computer program in accordance with claim 21 further comprising a code segment that highlights the orthogonal echo reflection area on the compounded image.

23. A computer program in accordance with claim 21 further comprising a code segment that tints the orthogonal echo reflection areas on the compounded image.

24. A computer program in accordance with claim 17 further comprising a code segment that backcalculates the echo reflection data to identify a source of the distal shadow.

25. A computer program in accordance with claim 17 further comprising a code segment that backcalculates the echo reflection data using an exponential algorithm.

* * * * *